United States Patent [19]

Ibach

[11] 4,392,854

[45] Jul. 12, 1983

[54] DEVICE FOR FIXING CATHETERS OR THE LIKE

[76] Inventor: Bernhard Ibach, Brüderstrasse 52, 5630 Remscheid, Fed. Rep. of Germany

[21] Appl. No.: 211,181

[22] Filed: Nov. 28, 1980

[51] Int. Cl.³ .................. A61M 5/00; A61M 25/00
[52] U.S. Cl. ........................ 604/174; 128/DIG. 26
[58] Field of Search ........... 128/133, 132 R, DIG. 26, 128/348, 207.14, 207.17

[56] References Cited

U.S. PATENT DOCUMENTS

| 2,443,140 | 6/1948 | Larsen | 128/132 R |
| 3,138,158 | 6/1964 | Gordon et al. | 128/133 |
| 3,674,032 | 7/1972 | Minganti | 128/132 R |
| 3,821,957 | 7/1974 | Riely et al. | 128/DIG. 26 |
| 3,976,080 | 8/1976 | Bornhorst et al. | 128/DIG. 26 |
| 4,209,015 | 6/1980 | Wicks | 128/DIG. 26 |
| 4,230,110 | 10/1980 | Beroff | 128/348 |

FOREIGN PATENT DOCUMENTS

| 64053 | 8/1955 | France | 128/132 R |
| 699253 | 11/1953 | United Kingdom | 128/DIG. 26 |

Primary Examiner—George F. Lesmes
Assistant Examiner—Nancy A. B. Swisher

[57] ABSTRACT

A device for fixing catheters or the like, having a curved plate with a reinforcing bead, and three supporting legs extending radially therefrom, the legs arranged to provide an access arc to the curved plate of greater than 180°.

5 Claims, 2 Drawing Figures

DEVICE FOR FIXING CATHETERS OR THE LIKE

BACKGROUND OF THE INVENTION

The invention relates to a device for fixing catheters or the like on the surface of human bodies by means of a plate or the like.

It is known to fix catheters by means of a plate on the body surface such that the plate rests on the body surface and is held fast by strips of plaster or the like, for example. It is not possible to sterilely provide the catheter outlet opening with a bandage without tension; the necessary frequent exchange of bandage each time is more difficult; during exchange, often the catheter is displaced from its optimum position and often it is damaged.

The invention provides a solution to the problem of providing a device for fixing catheters or the like which leaves the catheter outlet opening completely free to be accessible from all sides.

The problem is solved by inventively maintaining the plate or the like a distance from the body surface by a supporting device to be connected to the body.

What is guaranteed in this manner is that the catheter outlet opening on the body surface is not exposed to any compressive or tensile stresses; the device for fixing can easily be removed or exchanged.

SUMMARY OF THE INVENTION

Preferably, the supporting device consists of bent supports whose feet extend parallel to the body surface. The plate or the like and the supporting device can be made of synthetic material. At least the supporting device is usefully made of flexible material.

The plate or the like extends preferably normally to the body surface; the plate or the like can be curved; the plate or the like is preferably provided with holes or the like for receiving fastening threads for the catheter or the like.

According to an especially useful embodiment, there are provided three supports which are circularly but asymmetrically distributed about the plate; the three supports can be arranged in an arched angle of less than 180°.

BRIEF DESCRIPTION OF THE DRAWING

The drawing shows an exemplifying embodiment of the invention; hereinafter it will be described in more detail, it is shown in FIG. 1 is an exemplifying embodiment (side view)

DESCRIPTION OF THE PREFERRED EMBODIMENT

Figure 1:
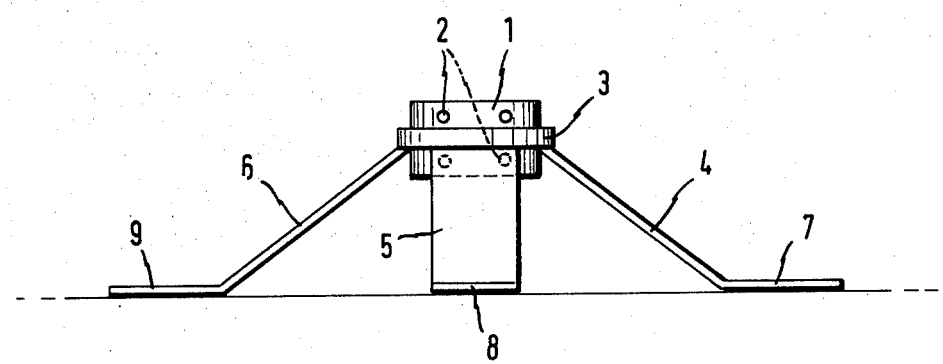

A curved plate 1 is provided, for example, with four holes 2 and has a reinforcing bead 3 which is attached to the outer side of the plate.

In the illustrated exemplifying embodiment, three supports 4, 5, 6 extend angularly from the reinforcing bead 3 and have feet 7, 8, 9 which when the device is used on the body of a human being are fastened, for example, by plaster.

Figure 2:
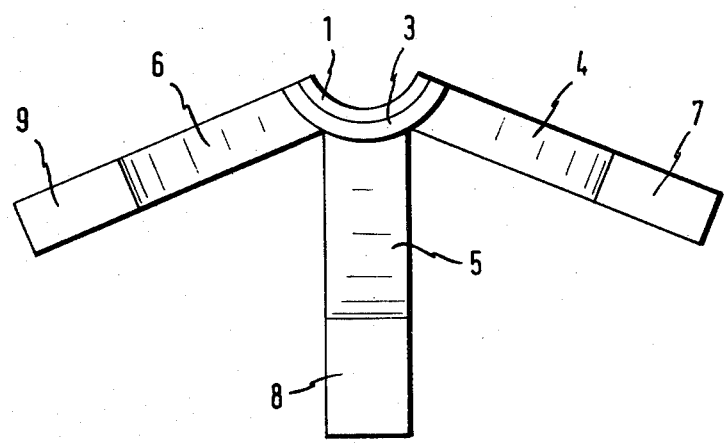
FIG. 2 is a top view of the exemplifying embodiment.

As can be seen from FIG. 2, the supports 4, 5, 6 extend radially from the plate 1 such that an arched angle greater than 180° is left free from supports. In this manner it is guaranteed that the catheter outlet opening is easily accessible from the free side; since the plate 1 by the angular supports 4 to 6 are maintained a distance from the body surface, said supports having in addition a certain flexibility, the catheter outlet opening is accessible all-around.

When being used, first the plate 1 is arranged, i.e. placed such that the concave side of the plate remains accessible in the most easy way.. Then the supporting feet 7 to 9 are attached on the body surface for example by strips of plaster and the catheter is attached to the plate 1. For this purpose, for example, two threads of surgical sewing material (3×0 silk) are placed around the catheter and are knotted. The two free thread ends are passed through the holes 2 and are knotted at least twice on the rear side of the plate 1.

Since the supporting device, as a result of the nature of its material, is slightly resilient, a semi-elastic fixing of the catheter is achieved; there is also the possibility to protect the catheter outlet opening by a bandage; the bandage can be exchanged without making necessary removal of the device for fixing the catheter. The catheter outlet opening at the body surface is not exposed to any compressive or tensile stress; it is completely free to be accessible from all sides; the device can without any difficulties be removed.

The inventive device for fixing can in principle be used in all those cases where a body surface having rather the same level is available; the main fields of application can for example be the fixing of suprapubic bladder catheters, nephrostomy catheters, pleuradrainages, central vein catheters, and oro- or nasotracheal tubes, particularly used for the artificial respiration of premature infants and babies.

One can use as material for manufacturing the device for fixing, for example, a flexible synthetic material commonly used for medical throw-away apparatus which fulfills the requirements of hygiene and safety.

I claim:

1. A device for fixing catheters or the like on the surface of a body, comprising a curved plate having an axis of curvature adapted for alignment substantially normal to said body, said curved plate extending less than 180° about said axis of curvature; and a plurality of legs attached to said curved plate, each of said legs extending at an acute angle relative to said axis of curvature and each of said legs having a foot portion adapted for adhesion to said body and a raised portion attached to said curved plate, to support said curved plate at a spaced-apart position from said body.

2. The device of claim 1, wherein said foot portion of said legs further comprise pads adapted for substantially horizontal alignment with said body.

3. The device of claim 2, wherein said plurality of legs further comprise three legs asymmetrically distributed about said curved plate.

4. The device of claim 3, wherein said asymmetrical distribution of said legs lies in an included angle about said curved plate of less than 180°.

5. The device of claim 1, wherein said curved plate further comprises a plurality of holes adapted for receiving fastening threads or the like.

* * * * *